United States Patent [19]

Hayakawa

[11] Patent Number: 6,066,763
[45] Date of Patent: May 23, 2000

[54] PROCESS FOR PREPARING FREE α-HYDROXY ACIDS FROM AMMONIUM SALTS THEREOF

[75] Inventor: Koichi Hayakawa, Hiratsuka, Japan

[73] Assignee: Nippon Soda Co., Ltd., Tokyo, Japan

[21] Appl. No.: 09/125,710

[22] PCT Filed: Feb. 25, 1997

[86] PCT No.: PCT/JP97/00528

§ 371 Date: Aug. 25, 1998

§ 102(e) Date: Aug. 25, 1998

[87] PCT Pub. No.: WO97/30962

PCT Pub. Date: Aug. 28, 1997

[30] Foreign Application Priority Data

Feb. 26, 1996 [JP] Japan ................................ 8-063672
Mar. 4, 1996 [JP] Japan ................................ 8-073230
Nov. 19, 1996 [JP] Japan ................................ 8-323411

[51] Int. Cl.[7] .................. C07C 381/00; C07C 59/08; C07C 65/01
[52] U.S. Cl. ............... 562/581; 562/465; 562/470; 562/579; 562/580; 562/589; 562/508; 562/471; 562/587; 562/588; 546/348; 548/565; 549/453
[58] Field of Search ................... 562/470, 465, 562/579, 580, 589, 508, 581, 471, 587, 588; 546/348; 548/565; 549/453

[56] References Cited

U.S. PATENT DOCUMENTS 4,212,994 7/1980 Wilson et al. ........................ 562/568

FOREIGN PATENT DOCUMENTS 0 040 254  11/1981  European Pat. Off. .
54-115317   9/1979  Japan ............................ C07C 57/04
63-264546  11/1988  Japan ............................ C07C 51/02
7-194387    8/1995  Japan ............................ C12P 7/56
7-330696   12/1995  Japan ........................... C07C 229/24
967352      8/1964  United Kingdom .

*Primary Examiner*—Rosalynd Keys
*Attorney, Agent, or Firm*—Jacobson, Price, Holman & Stern PLLC

[57] ABSTRACT

A process for preparing α-hydroxy acids by heating ammonium salts of α-hydroxy acids of general formula (I), removing the formed ammonia and water, adding water to the residue, and heating the obtained mixture, wherein R is hydrogen, $C_1$–$C_6$ alkyl, alkyl($C_1$–$C_6$)thioalkyl ($C_1$–$C_6$), phenyl or the like. This process is freed from the problem of disposal of by-products such as ammonium bisulfate and makes it possible to prepare a free α-hydroxy acid from an ammonium salt thereof economically and in a high yield.

[I]

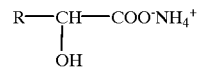

5 Claims, No Drawings

PROCESS FOR PREPARING FREE α-HYDROXY ACIDS FROM AMMONIUM SALTS THEREOF

TECHNICAL FIELD

This invention relates to processes for preparing α-hydroxy acids useful as starting materials for syntheses of various pharmaceuticals and agrochemicals and as additives to food and feed.

BACKGROUND ART

The conventional, most common method to chemically synthesize α-hydroxy acids is the hydrolysis of α-hydroxy nitrile with a mineral acid such as sulfuric acid. In this case, however, a salt of the mineral acid, such as hydrogen sulfate, of more than the equivalent is produced. The mineral acid salt should be treated, resulting in a problem of the disposal of a large amount of waste.

It is also known to obtain free α-hydroxy acids by a way that a metal salt or an ammonium salt of an α-hydroxy acid, which is produced by a biological process such as fermentation of a mixture containing sugar with a microorganism or the hydrolysis of α-hydroxy nitrile with a hydrolase produced by a microorganism, is reacted with a mineral acid such as sulfuric acid or treated with an ion exchange resin. In either process, a large quantity of mineral acid salts is produced, causing the same problem mentioned above.

A method known to produce no mineral acid salts, which become waste, is the esterification of an ammonium salt of an α-hydroxy acid with alcohol (Japanese Patent Laid-Open No. Hei 7-194387), followed by the hydrolysis of the obtained ester with an acid catalyst. This method is disadvantageous in using alcohol and an acid catalyst as additional additives. These additives should be recovered. Therefore it is not an advantageous process on an industrial scale.

There is another chemical synthetic method: hydrolysis of α-hydroxy nitrile with an inorganic base such as sodium hydroxide. In this case, a mineral acid or the like should be used to neutralize to give the target α-hydroxy acid. When doing so, the equivalent of a mineral acid salt is formed, causing the same problem of waste disposal.

Furthermore, the following processes are known to prepare corresponding free acids from ammonium salts of carboxylic acids: a small amount of water is added to an ammonium salt of an unsaturated fatty acid and the mixture is heated at total reflux at 80° C. or above in organic solvents in order to liberate and remove ammonia to give the unsaturated fatty acid (GB Patent Opened No. 967352); an organic solvent that forms an azeotropic mixture with water is added to a 10~50% aqueous solution of ammonium (meth)acrylate, and the resulting solution is heated to 60~100° C. to distil water as an azeotropic mixture and simultaneously remove ammonia in order to obtain free (meth)acrylic acid (Japanese Patent Laid-Open No. Sho 54-115317); and a 10–80% aqueous solution of an ammonium salt of an acidic amino acid is heated while water is added to it in order to distil out ammonia and water for producing the acidic amino acid (Japanese Patent Laid-Open No. Hei 7-330696).

In these methods, ammonia is easily removed in principle if the carboxylic acid has a high dissociation constant. Their disadvantages are, however, that the degree of dissociation of ammonium ions from ammonium salts of carboxylic acids is low for strong acids with pKa below 4, such as α-hydroxy acids. Therefore it is very difficult to remove ammonia from the strong acids. To remove most ammonia, a reaction should be carried out for a long period of time or it is necessary to add a large amount of organic solvents or a great quantity of water. The inventors of this invention have applied the above three methods to prepare α-hydroxy acids, and found them inappropriate as industrial processes because 50% or more of an ammonium salt of an α-hydroxy acid remained in each of the processes.

DISCLOSURE OF THE INVENTION

It is an object of this invention to provide processes for preparing free α-hydroxy acids from ammonium salts thereof in a high yield without creating a problem of waste disposal.

The present invention is a process for preparing α-hydroxy acids. The process consists of Step 1 of heating an ammonium salt of an α-hydroxy acid, represented by General Formula [I], with no solvents or in organic solvents and removing the formed ammonia and water, and Step 2 of successively adding water to the residue and heating the resulting mixture.

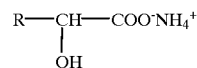
[I]

(wherein R is hydrogen, an alkyl which may have substituents, an alkenyl which may have substituents, a cycloalkyl which may have substituents, an alkoxy which may have substituents, an aryl which may have substituents, an aryloxy which may have substituents, a saturated heterocyclic group which may have substituents or an unsaturated heterocyclic group which may have substituents).

The present invention is described in detail in the following. α-Hydroxy acids, which are the object of this invention, are compounds represented by Formula [I]

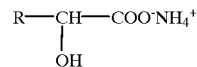
[I]

wherein R is hydrogen, an alkyl which may have substituents such as halogen, alkylthio, alkoxy or acyl; an alkenyl which may have substituents such as halogen, alkylthio, alkoxy or acyl; a cycloalkyl which may have substituents such as halogen, alkylthio, alkoxy or acyl; an alkoxy which may have substituents such as halogen, alkylthio, alkoxy or acyl; an aryl which may have substituents such as halogen, alkylthio, alkoxy or acyl; an aryloxy which may have substituents such as halogen, alkylthio, alkoxy or acyl; or a saturated or unsaturated heterocyclic group which may have substituents such as halogen, alkylthio, alkoy, or acyl.

Preferred groups include hydrogen, alkyl groups having 1 to 6 carbons, such as methyl, ethyl, propyl, isopropyl, butyl, isobutyl, t-butyl and pentyl; alkyl groups having 1 to 6 carbons (which may be substituted with halogen such as fluorine, chlorine or bromine, or with an alkylthio such as methylthio, ethylthio, propylthio, isopropylthio or butylthio); alkenyl groups having 2 to 6 carbons, such as vinyl, allyl, 2-butenyl and 3-butenyl; and 3 to 7 membered heterocyclic rings containing at least one of nitrogen, oxygen and sulfur as a non-carbon atom, such as phenyl, 2-pyridyl, 3-pyridyl, 4-pyridyl, 2-thienyl, 3-thienyl, 2-pyrrolyl, 3-pyrrolyl, 2-furyl and 3-furyl.

Examples of the α-hydroxy acids include glycolic acid, lactic acid, mandelic acid, α-hydroxy butyric acid, α-hydroxy isobutyric acid, α-hydroxy valeric acid, α-hydroxy isovaleric acid, α-hydroxy octanoic acid, α-hydroxy-3-butenoic acid, α-hydroxy-3-chloropropionic acid, α-hydroxy-4-methylthiobutyric acid, α-hydroxy-2-pyridylacetic acid, α-hydroxy-2-thienylacetic acid, α-hydroxy-2-pyrrolylacetic acid and α-hydroxy-2-furylacetic acid.

Ammonium salts of α-hydroxy acids can be produced by the hydrolysis of α-hydroxy nitrile with a hydrolase produced by a microorganism.

When an α-hydroxy acid is obtained as a metal salt by such a method as the hydrolysis of α-hydroxy nitrile with an inorganic base or a microorganism reaction, the metal salt can be converted to an ammonium salt, for example, by the same method as that disclosed in Japanese Patent Laid-Open No. Hei 7-194387: $NH_3$ and $CO_2$ are added to an aqueous solution of a metal salt of an α-hydroxy acid in order to convert to an ammonium salt of the α-hydroxy acid. The obtained ammonium salt can be used in the process of this invention.

This invention is a process consisting of the following two steps:

i) Step 1

An ammonium salt of an α-hydroxy acid is heated with no solvent or in organic solvents to remove water and ammonia, while converting it to poly-α-hydroxy acids with low molecular weight.

ii) Step 2

After most ammonia is removed (after Step 1 is completed), water is added to the reaction solution to heat for the hydrolysis of the poly-α-hydroxy acids with low molecular weight to give the free α-hydroxy acid.

Step 1 is heating an ammonium salt of an α-hydroxy acid to remove water and ammonia, while converting it to poly-α-hydroxy acids with low molecular weight. To do so, this reaction system may be under reduced pressure.

A variety of distillation equipment may be applicable in Step 1. In order to increase an evaporation area, equipment with a stirrer or to form a liquid film is particularly advantageous. Reaction temperature is usually in the range between 40 and 200° C., and the range between 60 and 170° C. is particularly preferred. A reaction is carried out under the pressure between 0.1 and 760 mmHg. The end point of the reaction is the time when the distillation of water and ammonia is finished. Remaining ammonia can be recycled as an ammonium salt of the α-hydroxy acid after the reaction is terminated. Therefore the reaction can be stopped before completion, if desired. When the target α-hydroxy acid is susceptible to oxidation, air may be replaced with an inert gas such as nitrogen, argon or helium so that the purity of the obtained α-hydroxy acid is improved. When a reaction is carried out at the atmospheric pressure, introducing an inert gas into the reaction solution improves the efficiency of removing ammonia.

Organic solvents applicable in Step 1 are those that do not react with α-hydroxy acids and ammonia and have a boiling point of 40° C. or above. Preferred are solvents forming an azeotropic mixture with water. Examples include benzene, toluene, xylene, mesitylene, ethylene glycol diethyl ether, ethylene glycol dimethyl ether, diethylene glycol dimethyl ether, diisobutyl ether, di-n-butyl ether, anisole and decane.

In the reaction of Step 1, α-hydroxy acid amide may be by-produced. This is because dissolved ammonia reacts with poly-α-hydroxy acids with low molecular weight to produce the amide. In this case, the rate of the by-product formed can be controlled under 2% by selecting proper organic solvents, adjusting the degree of pressure reduction or increasing an evaporation area. The said α-hydroxy acid amide is hydrolyzed to be the ammonium salt of the α-hydroxy acid in Step 2. Therefore the rate of the by-product formed is further reduced.

Ammonia distilled out in Step 1 can be recycled as ammonia gas and has a high utility value.

Step 2 is adding water to the reaction solution to heat, after the reaction of Step 1 is finished. Water is usually added 0.1~10 times (parts by weight), preferably 0.2~3 times (parts by weight), the weight of the still residue after the reaction of Step 1 is completed. Reaction temperature is 50~100° C. when a reaction is carried out at atmospheric pressure. A reaction may be conducted under pressure. With the use of a pressure-resistant reaction vessel, a reaction can be carried out at 100~300° C., preferably 120~170° C., so that a reaction time can be shortened.

During the reaction in Step 2, the poly-α-hydroxy acids with low molecular weight are hydrolyzed to be the α-hydroxy acid. The α-hydroxy acid amide by-produced in Step 1 is also partially hydrolyzed to be the ammonium salt of the α-hydroxy acid.

After the reaction is completed in Step 2, most of the α-hydroxy acid can be obtained as a free acid. Part of the acid may react with ammonia left in Step 1 and with ammonia produced by the hydrolysis of the by-produced α-hydroxy acid amide and remain as the ammonium salt of the α-hydroxy acid. The ammonium salt of the α-hydroxy acid, which is formed inside the system, can be recycled as a starting material in Step 1, causing no particular problems.

After the reaction is completed in Step 2, water is distilled out from the obtained aqueous solution of the α-hydroxy acid to give the free α-hydroxy acid with purity of 80% or more. To obtain a purer α-hydroxy acid, it is preferable to extract the solution with proper organic solvents, followed by the distillation of the solvents. Organic solvents insoluble in water and dissolving free α-hydroxy acids can be used for the extraction with no particular restrictions. Examples include toluene, ethyl acetate, methyl isobutyl ketone, n-butanol, diisopropyl ether and dichloroethane. Continuous extraction by countercurrent distribution may be employed for the extraction with organic solvents. This operation improves the recovery of a free α-hydroxy acid. If the target α-hydroxy acid is crystalline, the free acid can be precipitated in the aqueous solution after the reaction in Step 2 is completed and isolated by filtration, instead of the extraction with organic solvents.

It is possible to recycle the aqueous solutions, that is, the aqueous layers after the extraction with organic solvents or filtrates after the separation of crystals, as starting materials of Step 1 when they are concentrated, after a free α-hydroxy acid is obtained by the above-mentioned method.

EXAMPLES

The present invention is further described with reference to the following examples. α-Hydroxy acids, α-hydroxy acid amides and poly-α-hydroxy acids were analyzed by high performance liquid chromatography. Ammonia was determined by a UV absorbance measuring method using NADH~glutamic acid dehydrogenase (Methods of Enzymatic Analysis, Bergmeyer H. U. 3rd Edition, Vol. 8, pages 454~461).

Example 1

A rectifying tube was attached to a 100-ml flask equipped with a stirrer and a thermometer. A fractionating column equipped with a thermometer and a reflux condenser was connected to the tip of the rectifying tube. The fractionating column was set so that a distilled organic solvent was separated from distilled water and only the organic solvent was returned to the rectifying tube for reflux. Into this 100-ml flask were placed 14.20 g of an aqueous solution containing 53.40 mmol of ammonium (α-hydroxy-4-methylthiobutyrate and 40 ml of xylene. The flask was set in an oil bath of about 150° C. to heat the solution with stirring. In the beginning of the reaction, an azeotropic mixture of xylene and water rose to the top of the tube and the temperature at the top was 92° C.~93° C. With the progress of the reaction, water was distilled out separately. The temperature at the tube top gradually rose and reached the xylene boiling point of about 140° C. During the reaction, most ammonia, except that dissolved in distilled water, was discharged as gas from the tip of the reflux condenser. After the solution was heated at reflux for 4 hours, xylene was distilled out under reduced pressure to give 7.68 g of oil. The obtained oil was placed in an autoclave with an internal volume of about 60 ml. 20 ml of water was added to the oil to heat with stirring at about 150° C. for 4 hours. The internal pressure was approximately 3 kgf/cm² during heating. The reaction solution was cooled down to room temperature and transferred to a 50-ml round bottom flask. Water was distilled out under reduced pressure to give 9.56 g of oil. Analytical results are shown in Table 1. According to the results, the remaining rate of ammonia was 3.4%. The rate of by-produced α-hydroxy-4-methylthiobutyramide and the yield of free α-hydroxy-4-metylthiobutyric acid when dimers were taken into consideration for the calculation were 0.9% and 90.4%, respectively.

TABLE 1

|  | HMBA | HMB-Am | HMB-Di | $NH_4^+$ |
|---|---|---|---|---|
| Starting amount | 53.40 | 0.00 | 2.84 | 53.42 |
| Oil after reaction | 55.22 | 0.56 | 1.62 | 1.80 |

(Note)
Unit: mmol

TABLE 1-continued

|  | HMBA | HMB-Am | HMB-Di | $NH_4^+$ |
|---|---|---|---|---|

HMBA: α-hydroxy-4-methylthiobutyric acid
HMB-Am: α-hydroxy-4-methylthiobutyramide
HMB-Di: linear dimers of α-hydroxy-4-methylthiobutyric acid
$NH_4^+$: ammonium salt

Comparison Example 1

This example was performed according to the method disclosed in GB Patent No. 967352. Into a 50-ml flask equipped with a stirrer, a thermometer and a reflux condenser were placed 3.80 g of an aqueous solution containing 19.50 mmol of ammonium α-hydroxy-4-methylthiobutyrate and 1.0 ml of water to make a homogeneous solution. To the resulting solution was further added 23.0 ml of toluene. The flask was set in an oil bath of 120° C. to heat the solution at reflux with stirring. The temperature of the reaction solution was 100~103° C. and ammonia gas was generated from the top of the reflux condenser. After the solution was heated at reflux for 4 hours, toluene and water were distilled out under reduced pressure to give 3.82 g of oil. Analytical results are shown in Table 2. According to the results, the remaining rate of ammonia was 70.3%. The yield of free α-hydroxy-4-methylthiobutyric acid was 22.1% when dimers were taken into consideration.

TABLE 2

|  | HMBA | HMB-Am | HMB-Di | $NH_4^+$ |
|---|---|---|---|---|
| Starting amount | 19.50 | 0.00 | 1.28 | 20.10 |
| Oil after reaction | 19.02 | 0.49 | 1.69 | 14.14 |

(Note)
The unit and abbreviations of compounds are as described for Table 1.

Comparison Example 2

This example was performed according to the method disclosed in Japanese Patent Laid-Open No. Sho 54-115317. Into a 200-ml flask equipped with a stirrer, a thermometer, a single distilling column (10 mm in inner diameter and 10 cm high) and a condenser were placed a 50% by weight aqueous solution containing 25.88 mmol of ammonium α-hydroxy-4-methylthiobutyrate and 115 ml of toluene. The resulting solution was heated with stirring, while a small amount of dried air was being introduced into the vapor phase. Ammonia gas was generated simultaneously when an azeotropic mixture of toluene and water was distilled out. The distillation of the azeotropic mixture stopped about 40 minutes after the distillation started. The reaction was terminated approximately 10 minutes after almost only toluene was distilled out. The total amount of the distilled solution was 64.5 g. The total amount of the solution after the reaction was 58.8 g. The solution after the reaction was condensed under reduced pressure to give 5.6 g of oil. Analytical results are shown in Table 3. According to the results, the remaining rate of ammonia was 56.6%. The yield of free α-hydroxy-4-methylthiobutyric acid was 32.8% when dimers were taken into consideration.

TABLE 3

|  | HMBA | HMB-Am | HMB-Di | $NH_4^+$ |
|---|---|---|---|---|
| Starting amount | 25.88 | 0.00 | 1.75 | 27.35 |
| Oil after condensation | 25.10 | 0.15 | 2.59 | 15.47 |

(Note)
The unit and abbreviations of compounds are as described for Table 1.

Comparison Example 3

This example was performed according to the method disclosed in Japanese Patent Laid-Open No. Hei 7-330696. Into a 50-ml flask equipped with a stirrer, a thermometer, a dropping funnel, a single distilling column (10 mm in inner diameter and 10 cm high) and a condenser were placed 10.35 g of an aqueous solution containing 51.81 mmol of ammonium α-hydroxy-4-methylthiobutyrate and 12 ml of water. Water preheated to 70° C. was supplied into the flask continuously at 20 ml/hour while a very small amount of nitrogen was flowing from a capillary into the flask at the atmospheric pressure. The bottom flask was heated in an oil bath of 150° C. Aqueous ammonia was distilled at the top distillation temperature of 99~100° C. at a distillation speed of 20 ml/hour, while an amount of the retentive solution was roughly kept constant. A total of about 80 ml of aqueous ammonia was obtained over approximately 4 hours. The total amount of the solution after the reaction was 21.9 ml. Analytical results are shown in Table 4. According to the results, the remaining rate of ammonia was 70.8%. The yield of free α-hydroxy4-methylthiobutyric acid was 21.9% when dimers were taken into consideration.

TABLE 4

|  | HMBA | HMB-Am | HMB-Di | $NH_4^+$ |
|---|---|---|---|---|
| Starting amount | 51.81 | 0.00 | 3.50 | 54.75 |
| Solution after reaction | 51.65 | 0.00 | 1.70 | 38.78 |

(Note)
The unit and abbreviations of compounds are as described for Table 1.

Example 2

A 100-ml flask was equipped with the same devices as those used in Example 1. In the flask were placed 5.84 g of an aqueous solution containing 45.61 mmol of ammonium lactate and 40 ml of xylene. The flask was set in an oil bath of about 150° C. to heat the solution with stirring. In the beginning of the reaction, an azeotropic mixture of xylene and water rose to the top of the tube and the temperature at the top was 92~93° C. With the progress of the reaction, water was distilled out separately. The temperature at the tube top gradually rose and reached the xylene boiling point of about 140° C. During the reaction, most ammonia, except that dissolved in distilled water, was discharged as gas from the top of the reflux condenser. The solution was heated at reflux with stirring for a total of 4 hours, while the reaction proceeded as described above. Xylene was then distilled out under reduced pressure to give 4.08 g of oil. The obtained oil was placed in an autoclave with an internal volume of about 60 ml. 20 ml of water was added to the oil to heat with stirring at about 150° C. for 4 hours. The internal pressure was approximately 3 kgf/cm² during heating. The reaction solution was cooled down to room temperature and transferred to a 50-ml round bottom flask. Water was distilled out under reduced pressure to give 4.52 g of oil. Analytical results are shown in Table 5. According to the results, the remaining rate of ammonia was 7.6%. The rate of by-produced lactamide was 1.2%. The yield of free lactic acid was 89.9%.

TABLE 5

|  | LA | LA-Am | $NH_4^+$ |
|---|---|---|---|
| Starting amount | 45.61 | 0.00 | 45.63 |
| Oil after condensation | 45.04 | 0.56 | 3.48 |

(Note)
Unit: mmol
LA: Lactic acid
LA-Am: Lactamide

Example 3

A 100-ml flask was equipped with the same devices as those used in Example 1. In the flask were placed 10.46 g of an aqueous solution containing 58.78 mmol of ammonium mandelate and 40 ml of xylene. The flask was set in an oil bath of about 150° C. to heat the solution with stirring. In the beginning of the reaction, an azeotropic mixture of xylene and water rose to the top of the tube and the temperature at the top was 92~93° C. With the progress of the reaction, water was distilled out separately. The temperature at the tube top gradually rose and reached the xylene boiling point of about 140° C. During the reaction, most ammonia was discharged as gas from the top of the reflux condenser. The solution was heated at reflux with stirring for a total of 4 hours, while the reaction proceeded as described above. Xylene was then distilled out under reduced pressure to give 7.38 g of oil. The obtained oil was placed in an autoclave with an internal volume of about 60 ml. 20 ml of water was added to the oil to heat with stirring at about 150° C. for 4 hours. The internal pressure was approximately 3 kgf/cm² during heating. The reaction solution was cooled down to room temperature and transferred to a 50-ml round bottom flask. Water was distilled out under reduced pressure to give 9.63 g of oil. Analytical results are shown in Table 6. According to the results, the remaining rate of ammonia was 2.8%. The rate of by-produced mandelamide was 1.8%. The yield of free mandelic acid was 93.5%.

TABLE 6

|  | MA | MA-Am | $NH_4^+$ |
|---|---|---|---|
| Starting amount | 58.78 | 0.00 | 58.81 |
| Crystals after condensation | 57.68 | 1.07 | 1.67 |

(Note)
Unit: mmol

TABLE 6-continued

| | MA | MA-Am | NH$_4^+$ |
|---|---|---|---|
MA: Mandelic acid
MA-Am: Mandelamide

Example 4

A 100-ml flask was equipped with the same devices as those used in Example 1. In the flask were placed 10.01 g of an aqueous solution containing 43.24 mmol of ammonium α-hydroxy-4-methylthiobutyrate and 50 ml of anisole. The flask was set in an oil bath of about 170° C. to heat the solution with stirring. With the progress of the reaction, water was distilled out separately. The temperature at the tube top gradually rose and reached the anisole boiling point of about 156° C. During the reaction, most ammonia, except that dissolved in the distilled water, was discharged as gas from the top of the reflux condenser. The solution was heated at reflux for 4 hours. Anisole was then distilled out under reduced pressure to give 6.78 g of oil. The obtained oil was placed in an autoclave with an internal volume of about 60 ml. 20 ml of water was added to the oil to heat with stirring at about 150° C. for 4 hours. The internal pressure was approximately 3 kgf/cm$^2$ during heating. The reaction solution was cooled down to room temperature and transferred to a 50-ml round bottom flask. Water was distilled out under reduced pressure to give 7.61 g of oil. Analytical results are shown in Table 7. According to the results, the remaining rate of ammonia was 3.7%. The rate of by-produced α-hydroxy-4-methylthiobutyramide and the yield of free α-hydroxy-4-methylthiobutyric acid when dimers were taken into consideration for the calculation were 1.0% and 90.1%, respectively.

TABLE 7

| | HMBA | HMB-Am | HMB-Di | NH$_4^+$ |
|---|---|---|---|---|
| Starting amount | 43.24 | 0.00 | 1.50 | 44.74 |
| Oil after reaction | 43.32 | 0.45 | 1.22 | 1.64 |

(Note)
The unit and abbreviations of compounds are as described for Table 1.

Example 5

A 100-ml flask was equipped with the same devices as those used in Example 1. In the flask were placed 10.12 g of an aqueous solution containing 43.72 mmol of ammonium α-hydroxy-4-methylthiobutyrate and 50 ml of ethylene glycol diethyl ether. The flask was set in an oil bath of about 150° C. to heat the solution with stirring. With the progress of the reaction, water was distilled out separately. The temperature at the tube top gradually rose and reached the boiling point of ethylene glycol diethyl ether of about 121° C. During the reaction, most ammonia, except that dissolved in the distilled water, was discharged as gas from the top of the reflux condenser. The solution was heated at reflux for 4 hours. Ethylene glycol diethyl ether was then distilled out under reduced pressure to give 6.94 g of oil. The obtained oil was placed in an autoclave with an internal volume of about 60 ml. 20 ml of water was added to the oil to heat with stirring at about 150° C. for 4 hours. The internal pressure was approximately 3 kgf/cm$^2$ during heating. The reaction solution was cooled down to room temperature and transferred to a 50-ml round bottom flask. Water was distilled out under reduced pressure to give 7.58 g of oil. Analytical results are shown in Table 8. According to the results, the remaining rate of ammonia was 3.8%. The rate of by-produced α-hydroxy-4-methylthiobutyramide and the yield of free α-hydroxy-4-methylthiobutyric acid when dimers were taken into consideration for the calculation were 1.1% and 90.9%, respectively.

TABLE 8

| | HMBA | HMB-Am | HMB-Di | NH$_4^+$ |
|---|---|---|---|---|
| Starting amount | 43.72 | 0.00 | 1.52 | 45.24 |
| Oil after reaction | 44.24 | 0.47 | 1.01 | 1.74 |

(Note)
The unit and abbreviations of compounds are as described for Table 1.

Example 6

A straight tube was attached to a 50-ml flask equipped with a stirrer, a thermometer and a gas introducing tube. A fractionating column equipped with a thermometer and a reflux condenser was connected to the tip of the straight tube. In the 50-ml flask were placed 5.09 g of an aqueous solution containing 20.61 mmol of ammonium α-hydroxy-4-methylthiobutyrate and 20 ml of diethylene glycol dimethyl ether. The flask was set in an oil bath of about 145° C. to heat the solution with stirring. While heating, nitrogen gas was introduced into the reaction solution at the speed of 100 ml/min in order to distil out water already present in the starting materials and water produced during the reaction, as an azeotropic mixture with diethylene glycol dimethyl ether, to the outside of the reaction system. Most ammonia produced during the reaction, except that dissolved in the distilled water, was discharged as gas from the top of the reflux condenser. The temperature of the reaction solution was approximately 115° C. in the beginning of the reaction due to the presence of a lot of water. With the progress of the reaction, the temperature gradually rose to be constant at nearly 130° C. After the reaction was carried out for 2 hours, diethylene glycol dimethyl ether was distilled out under reduced pressure to give 3.65 g of oil. The obtained oil was transferred to a 50-ml round bottom flask. 20 ml of water was added to the oil to heat with stirring at reflux for 4 hours at 100° C. The reaction solution was cooled down to room temperature and analyzed. The analytical results are shown in Table 9. According to the results, the remaining rate of ammonia was 4.3%. The rate of by-produced α-hydroxy-4-methylthiobutyramide and the yield of free α-hydroxy-4-methylthiobutyric acid when dimers were taken into consideration for the calculation were 1.1% and 92.7%, respectively.

TABLE 9

|  | HMBA | HMB-Am | HMB-Di | $NH_4^+$ |
|---|---|---|---|---|
| Starting amount | 20.61 | 0.00 | 0.61 | 21.22 |
| Oil after reaction | 21.16 | 0.24 | 0.21 | 0.92 |

(Note)
The unit and abbreviations of compounds are as described for Table 1.

Example 7

A straight tube was attached to a 50-ml flask equipped with a stirrer and a thermometer. A fractionating column equipped with a thermometer and a reflux condenser was connected to the tip of the straight tube. The top of the reflux condenser was connected to a tap aspirator so that the inside of the reaction system was under reduced pressure. In the 50-ml flask were placed 5.00 g of an aqueous solution containing 20.25 mmol of ammonium α-hydroxy-4-methylthiobutyrate and 25 ml of diethylene glycol dimethyl ether, The flask was set in an oil bath of about 110° C. to heat the solution with stirring. While heating, the pressure inside the reaction system was adjusted to 600~650 mmHg by the tap aspirator in order to distil out water already present in the starting materials and water produced during the reaction, as an azeotropic mixture with diethylene glycol dimethyl ether, to the outside of the reaction system. Most ammonia produced during the reaction, except that dissolved in the distilled water, was absorbed by the aspirator as gas. The temperature of the reaction solution was approximately 90~93° C. in the beginning of the reaction. With the progress of the reaction, the temperature gradually rose to be constant at nearly 100° C. After the reaction was carried out for 4 hours, diethylene glycol dimethyl ether was distilled out under reduced pressure to give 4.08 g of oil. The obtained oil was transferred to a 50-ml round bottom flask. 20 ml of water was added to the oil to heat with stirring at reflux for 4 hours at 100° C. The reaction solution was cooled down to room temperature and analyzed. The analytical results are shown in Table 10. According to the results, the remaining rate of ammonia was 1.1%. The rate of by-produced α-hydroxy-4-methylthiobutyramide and the yield of free α-hydroxy-4-methylthiobutyric acid when dimers were taken into consideration for the calculation were 1.9% and 93.4%, respectively.

TABLE 10

|  | HMBA | HMB-Am | HMB-Di | $NH_4^+$ |
|---|---|---|---|---|
| Starting amount | 20.25 | 0.00 | 0.60 | 20.85 |
| Oil after reaction | 20.26 | 0.40 | 0.53 | 0.22 |

(Note)
The unit and abbreviations of compounds are as described for Table 1.

Example 8

9.18 g of an aqueous solution containing 45.95 mmol of ammonium α-hydroxy-4-methylthiobutyrate was placed in a 50-ml round bottom flask. The solution was heated at 120~125° C. and 0.8~1.5 mmHg for 4 hours in a rotary evaporator in order to remove generated ammonia and water. The total amount of the remaining reaction solution was 7.29 g. The solution contained 3.06 mmol of ammonium α-hydroxy-4-methylthiobutyrate and 0.87 mmol of α-hydroxy-4-methylthiobutyramide, besides poly-α-hydroxy-4-methylthiobutyric acids. 22 ml of water was added to the remaining solution obtained after the reaction. The resulting solution was heated at reflux at the atmospheric pressure for 20 hours. The reaction solution was cooled down to room temperature, and extracted with 25 ml of methyl isobutyl ketone 3 times. The organic layers were combined and concentrated to give 7.08 g of oil. The aqueous layer after the extraction was also concentrated to give 0.81 g of oil. Analytical results are shown in Table 11. According to the results, the remaining rate of ammonia was 7.0%. The rate of by-produced α-hydroxy-4-methylthiobutyramide and the yield of free α-hydroxy-4-methylthiobutyric acid when dimers were taken into consideration for the calculation were 1.0% and 81.9%, respectively.

TABLE 11

|  | HMBA | HMB-Am | HMB-Di | $NH_4^+$ |
|---|---|---|---|---|
| Starting amount | 45.95 | 0.00 | 3.10 | 48.56 |
| Oil from organic layers | 42.68 | 0.40 | 1.13 | 0.00 |
| Oil from aqueous layer | 3.46 | 0.11 | 0.00 | 3.41 |

(Note)
The unit and abbreviations of compounds are as described for Table 1.

Example 9

9.25 g of an aqueous solution containing 46.31 mmol of ammonium α-hydroxy-4-methylthiobutyrate was placed in a 50-ml round bottom flask. The solution was heated at 135~140° C. and 0.8~1.5 mmHg for 4 hours in a rotary evaporator in order to remove generated ammonia and water. The total amount of the remaining reaction solution was 7.20 g. The solution contained 2.54 mmol of ammonium α-hydroxy-4-methylthiobutyrate and 0.57 mmol of α-hydroxy-4-methylthiobutyramide, besides poly-α-hydroxy-4-methylthiobutyric acids. The remaining solution obtained after the reaction was transferred to an autoclave with an internal volume of about 60 ml. 20 ml of water was added to the solution to heat in an oil bath of 170~175° C. for 4 hours. The internal pressure was 3 kgf/cm² during heating. The reaction solution was cooled down to room temperature, and transferred to a 50-ml round bottom flask. Water was distilled out under reduced pressure to give 7.45 g of oil. Analytical results are shown in Table 12. According to the results, the remaining rate of ammonia was 6.2%. The rate of by-produced α-hydroxy-4-methylthiobutyramide and the yield of free α-hydroxy-4-methylthiobutyric acid when dimers were taken into consideration for the calculation were 0.4% and 83.2%, respectively.

TABLE 12

|  | HMBA | HMB-Am | HMB-Di | $NH_4^+$ |
|---|---|---|---|---|
| Starting amount | 46.31 | 0.00 | 3.12 | 48.93 |
| Oil after reaction | 46.78 | 0.23 | 0.85 | 3.04 |

(Note)
The unit and abbreviations of compounds are as described for Table 1.

Example 10

9.04 g of an aqueous solution containing 79.58 mmol of ammonium lactate was placed in a 50-ml round bottom flask. The solution was heated at 118~120° C. and 11~14 mmHg for 6 hours in a rotary evaporator in order to remove generated ammonia and water. The total amount of the remaining reaction solution was 6.62 g. The solution contained 6.31 mmol of ammonium lactate and 1.04 mmol of lactamide, besides polylactic acids. The remaining solution obtained after the reaction was transferred to an autoclave with an internal volume of about 60 ml. 30 ml of water was added to the solution to heat in an oil bath of 150~155° C. for 3 hours. The internal pressure was 3 kgf/cm² during heating. The reaction solution was cooled down to room temperature, transferred to a 50-ml round bottom flask, and concentrated under reduced pressure so that the solution was an about 80% aqueous solution. 9.11 g of oil was obtained. Analytical results are shown in Table 13. According to the results, the remaining rate of ammonia was 8.9%. The yield of free lactic acid to the starting amount of ammonium lactate was 90.1%.

TABLE 13

|  | LA | LA-Am | $NH_4^+$ |
|---|---|---|---|
| Starting amount | 79.58 | 0.00 | 80.13 |
| Oil after reaction | 78.91 | 0.58 | 7.17 |

(Note)
The unit and abbreviations of compounds are as described for Table 5.

Example 11

9.06 g of an aqueous solution containing 45.84 mmol of ammonium mandelate was placed in a 50-ml round bottom flask. The solution was heated at 118~120° C. and 0.5~1.0 mmHg for 4 hours in a rotary evaporator in order to remove generated ammonia and water. The total amount of the remaining reaction solution was 6.09 g. The solution contained 1.38 mmol of ammonium mandelate and 0.49 mmol of mandelamide, besides poly-mandelic acids. The remaining solution obtained after the reaction was transferred to an autoclave with an internal volume of about 60 ml. 20 ml of water was added to the solution to heat in an oil bath of 170~175° C. for 4 hours. The internal pressure was 3 kgf/cm² during heating. The reaction solution was cooled down to room temperature, and transferred to a 50-ml round bottom flask. Water was distilled out under reduced pressure to give 6.92 g of crystals. Analytical results are shown in Table 14. According to the results, the remaining rate of ammonia was 3.6%. The yield of free mandelic acid to the starting amount of ammonium mandelate was 92.9%.

TABLE 14

|  | MA | MA-Am | $NH_4^+$ |
|---|---|---|---|
| Starting amount | 45.84 | 0.00 | 46.79 |
| Oil after reaction | 44.24 | 0.19 | 1.67 |

(Note)
The unit and abbreviations of compounds are as described for Table 6.

[Effects of the Invention]

The processes of this invention are preferable and advantageous from an industrial viewpoint with the various reasons described in the following:

1. When a free α-hydroxy acid is produced from an ammonium salt thereof, ammonia is removed as ammonia gas so that ammonium salt waste is not produced.
2. The processes are advantageous in production cost thanks to no addition of additional substances, such as catalysts or additives for neutralization.
3. Remaining ammonia and by-produced α-hydroxy acid amide can be separated from a free α-hydroxy acid and recycled, as an ammonium salt thereof after a hydrolytic reaction is carried out.

Industrial Use

The present invention, as described above, is a process for preparing a free α-hydroxy acid from an ammonium salt thereof advantageously and efficiently on an industrial scale so as to have great industrial significance.

What is claimed:

1. A process for preparing an α-hydroxy acid in which an ammonium salt of the α-hydroxy acid, represented by Formula I, is heated, ammonia and water are evolved and removed to leave a residue containing poly-α-hydroxy acids of low molecular weight, water is then added to the residue, and a resulting mixture is heated to convert the poly-α-hydroxy acids to free α-hydroxy acid, wherein Formula I is:

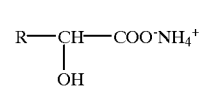

I wherein R is hydrogen, an alkyl which may have substituents, an alkenyl which may have substituents, a cycloalkyl which may have substituents, an alkoxy which may have substituents, an aryl which may have substituents, an aryloxy which may have substituents, a saturated heterocyclic group which may have substituents or an unsaturated heterocyclic group which may have substituents.

2. A Process for preparing an α-hydroxy acid in which an ammonium salt of the α-hydroxy acid, represented by Formula I, is heated under reduced pressure, ammonia and water are evolved and removed to leave a residue containing poly-α-hydroxy acids of low molecular weight, water is then added to the residue, and a resulting mixture is heated to convert the poly-α-hydroxy acids to free α-hydroxy acid, wherein Formula I is:

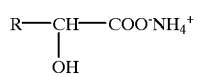

wherein R is hydrogen, an alkyl which may have substituents, an alkenyl which may have substituents, a cycloalkyl which may have substituents, an alkoxy which may have substituents, an aryl which may have substituents, an aryloxy which may have substituents, a saturated heterocyclic group which may have substituents or an unsaturated heterocyclic group which may have substituents.

3. A process for preparing an α-hdyroxy acid in which an ammonium salt of the α-hydroxy acid, represented by Formula I, is heated in an organic solvent, ammonia and water are evolved and removed to leave a residue containing poly-α-hydroxy acids of low molecular weight, water is then added to the residue, and a resulting mixture is heated to convert the poly-α-hydroxy acids to free α-hydroxy acid, wherein Formula I is:

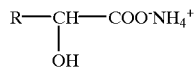

wherein R is hydrogen, an alkyl which may have substituents, an alkenyl which may have substituents, a cycloalkyl which may have substituents, an alkoxy which may have substituents, an aryl which may have substituents, an aryloxy which may have substituents, a saturated heterocyclic group which may have substituents or an unsaturated heterocyclic group which may have substituents.

4. A process for preparing an α-hydroxy acid in which an ammonium salt of the α-hydroxy acid, represented by Formula I, is heated, ammonia and water are evolved and removed to leave a residue containing poly-α-hydroxy acids of low molecular weight, water is then added to the residue, and a resulting mixture is heated to convert the poly-α-hydroxy acids to free α-hydroxy acid, wherein Formula I is:

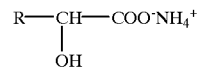

wherein R is hydrogen, an alkyl having 1 to 6 carbons which may be substituted with halogen or an alkylthio having 1 to 6 carbons, an alkenyl having 2 to 6 carbons, phenyl, 2-pyridyl, 3-pyridyl, 4-pyridyl, 2-thienyl, 3-thienyl, 2-pyrrolyl, 3-pyrrolyl, 2-furyl or 3-furyl.

5. A process for preparing an α-hydroxy acid in which an ammonium salt of the α-hydroxy acid, represented by Formula I, is heated, ammonia and water are evolved and removed to leave a residue containing poly-α-hydroxy acids of low molecular weight, water is then added to the residue, and a resulting mixture is heated to convert the poly-α-hydroxy acids to free α-hydroxy acid, wherein Formula I is:

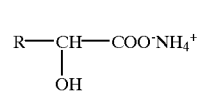

wherein R is hydrogen, an alkyl having 1 to 6 carbons, a $C_1$–$C_6$ alkylthio $C_1$–$C_6$ alkyl, or phenyl.

* * * * *